US008815243B2

(12) United States Patent
Lee et al.

(10) Patent No.: US 8,815,243 B2
(45) Date of Patent: Aug. 26, 2014

(54) PHARMACEUTICAL COMPOSITION WITH ANTIBODY THAT BINDS TO HEAT SHOCK PROTEIN 27(HSP270) AND METHOD FOR PROMOTING WOUND HEALING

(75) Inventors: Yoon Jin Lee, Mapo-gu (KR); Yun-Sil Lee, Nowon-gu (KR); Hae-June Lee, Hwaseong-si (KR); Seo-Hyun Choi, Eunpyeong-gu (KR); Kyeng-Jung Kim, Seoul (KR)

(73) Assignee: Korea Institute of Radiological & Medical Sciences, Seoul (KR)

( * ) Notice: Subject to any disclaimer, the term of this patent is extended or adjusted under 35 U.S.C. 154(b) by 0 days.

(21) Appl. No.: 13/817,760

(22) PCT Filed: Aug. 18, 2011

(86) PCT No.: PCT/KR2011/006065
§ 371 (c)(1),
(2), (4) Date: Feb. 19, 2013

(87) PCT Pub. No.: WO2012/023810
PCT Pub. Date: Feb. 23, 2012

(65) Prior Publication Data
US 2013/0156787 A1   Jun. 20, 2013

(30) Foreign Application Priority Data

Aug. 18, 2010  (KR) .................. 10-2010-0079857

(51) Int. Cl.
*C07K 16/18*   (2006.01)
*C07K 14/435*  (2006.01)
*C07K 16/44*   (2006.01)
*A61K 39/395*  (2006.01)

(52) U.S. Cl.
CPC ........... *A61K 39/3955* (2013.01); *A61K 39/395* (2013.01)
USPC ................... 424/152.1; 424/130.1; 424/141.1

(58) Field of Classification Search
None
See application file for complete search history.

(56) References Cited

U.S. PATENT DOCUMENTS 4,816,567 A    3/1989 Cabilly et al.
2007/0122414 A1*  5/2007 Georges et al. ............ 424/155.1

FOREIGN PATENT DOCUMENTS

KR    10-2009-0010662 A    1/2009

OTHER PUBLICATIONS

Yu et al., Investigative Ophthalmology & Visual Science 49(2): 522-527, Feb. 2008.*
Witte et al., Cancer and Metastasis Reviews 17: 155-161, 1998.*
Riemer et al., Mol. Immunol. 42: 1121-1124, 2005.*
Stancovski et al., Proceedings of the National Academy of Science USA 88: 8691-8695, 1991.*
Banerjee et al., "Heat Shock Protein 27 (Hsp27) Induces Tolerogenic and Pro-angiogenic Macrophages: A Novel Immune Escape Mechanism in Human Breast Cancer," Abstracts OR.95, doi:10.1016/j.clim. 2009.03.110, 1 page (2009).
Clackson et al., "Making antibody fragments using phage display libraries," *Letters to Nature*, 352:624-628 (1991).
Eguchi et al., "Proteomic analysis of hypoxia-induced tube breakdown of an in vitro capillary model composed of HUVECs: Potential role of p38-regulated reduction of HSP27," *Proteomics*, 8:2897-2906 (2008).
Evans et al., "Vascular endothelial growth factor induces heat shock protein (HSP) 27 serine 82 phosphorylation and endothelial tubologenesis via protein kinase D and independent of p38 kinase," *Elsevier*, Cellular Signalling 20:1375-1884 (2008).
"Heat shock protein beta-1 [*Homo sapiens*]," http://www.ncbi.nlm.nih.gov/protein/NP_001531.1, 7 pages (2013).
Hirano et al., "HSP27 regulates fibroblast adhesion, motility, and matrix contraction," *Cell Stress & Chaperones*, 9(1):29-37 (2004).
International Search Report and Written Opinion of the International Searching Authority, mailed Mar. 28, 2012, for corresponding International Application No. PCT/KR2011/006065, 8 pages.
Köhler et al., "Derivation of specific antibody-producting tissue culture and tumor lines by cell fusion," *Eur. J. Immunol.*, 6:511-519 (1976).
Kwon et al., "Protective effect of heat shock protein 27 using protein transduction domain-mediated delivery on ischemia/reperfusion heart injury," *Elsevier*, Biochemical and Biophysical Research Communications 363:399-404 (2007).
Lee et al., "HSP25 inhibits radiation-induced apoptosis through reduction of PKCδ-mediated ROS production," *Oncogene*, 24:3715-3725 (2005).
Marks et al., "By-passing Immunization Human Antibodies from V-gene Libraries Displayed on Phage," *J. Mol. Biol.*, 222:581-597 (1991).

(Continued)

*Primary Examiner* — Phuong Huynh
(74) *Attorney, Agent, or Firm* — Klarquist Sparkman, LLP (57) ABSTRACT

The present invention relates to a pharmaceutical composition for promoting angiogenesis, containing an antibody that specifically binds to heat shock protein (HSP) 27. In addition, the present invention relates to a pharmaceutical composition containing an antibody that specifically binds to HSP 27, for treating an angiogenesis-dependent ailment selected from a group consisting of a wound, chronic ulcer, ischemic stroke, myocardial infarction, angina pectoris, and cerebrovascular dementia. In addition, the present invention relates to a method for promoting the in vitro growth of endothelial cells using an antibody that specifically binds to HSP27. In addition, the present invention relates to a method for screening for active substances for promoting angiogenesis or for active substances for treating an angiogenesis-dependent ailment, the method comprising the following steps: treating vascular endothelial cell lines with each specimen; measuring the content of HSP27 in the respective vascular endothelial cell lines; and selecting a specimen in which the HSP27 content in the vascular endothelial cell lines are decreased as compared to a control group.

8 Claims, 6 Drawing Sheets

(56) References Cited

OTHER PUBLICATIONS

Martin-Ventura et al., "Biological Significance of Decreased HSP27 in Human Atherosclerosis," *Arteriosclerosis, Thrombosis, and Vascular Biology*, 26:1337-1343, http://atvb.ahajournals.org/content/26/6/1337 (2006).

Office Action for related Korean Patent Application No. 10-2010-0079857, 6 pages, Jun. 5, 2012.

Notice of Allowance for related Korean Patent Application No. 10-2010-0079857, 7 pages, Dec. 27, 2012.

Papapetropoulos et al., "Hydrogen sulfide is an endogenous stimulator of angiogenesis," *PNAS*, 106(51):21972-21977 (2009).

Trott et al., "Effect of phosphorylated hsp27 on proliferation of human endothelial and smooth muscle cells," *Proteomics*, 9:3383-3394 (2009).

\* cited by examiner

PHARMACEUTICAL COMPOSITION WITH ANTIBODY THAT BINDS TO HEAT SHOCK PROTEIN 27(HSP270) AND METHOD FOR PROMOTING WOUND HEALING

CROSS-REFERENCE TO RELATED APPLICATIONS

This application is the U.S. National Stage of International Application No. PCT/KR2011/006065, filed Aug. 18, 2011, which claims priority to and the benefit of Korean Patent Application No. 10-2010-0079857, filed Aug. 18, 2010, which is hereby incorporated by reference in its entirety.

TECHNICAL FIELD

The present invention relates to a pharmaceutical composition for promoting angiogenesis and a method for screening for active substances for promoting angiogenesis, and more particularly, to a pharmaceutical composition for promoting angiogenesis including a material that suppresses a function of a heat shock protein (HSP), which is revealed as to impede growth of vascular endothelial cells, a pharmaceutical composition for treating an angiogenesis-dependent ailment, a method of screening active substances for promoting angiogenesis by selecting the material suppressing HSP, and a method of screening active substances for treating an angiogenesis-dependent ailment by selecting the material suppressing HSP.

BACKGROUND ART

Angiogenesis is a process of forming new capillaries as endothelial cells of pre-existing blood vessels decompose, extracellular matrix, migrate, divide, and differentiate to form forming new capillaries, which may occur during a physiological process, such as growth, reproduction, or healing wounds. Also, angiogenesis is related to pathological states, such as tumor growth, arthritis, diabetes. Angiogenesis requires a complicated series of processes including growth, migration, and differentiation of vascular endothelial cells, capillary formation, or the like, and many angiogenesis promoting factors and angiogenesis suppressing factors in the process have been discovered. The angiogenesis suppressing factors are activated to counteract the angiogenesis promoting factors. Since toxicity of angiogenesis suppressants naturally present in a body is low, the angiogenesis suppressants may be used to suppress pathological angiogenesis, and thus many medications related to the angiogenesis suppressants are under development.

Excessive formation of blood vessels may become a main cause of worsening a disease, but non-formation of blood vessels also causes a serious disease. Angiogenesis is a necessary phenomenon for healing wounds or regenerating tissue, and thus, for example, a placenta with undeveloped angiogenesis becomes an important cause of miscarriage, and necrosis, ulceration, and ischemia due to the non-formation of blood vessels may cause dysfunction of the tissue or organ, or may cause death. Moreover, unsmooth flow of blood is a cause of diseases, such as arteriosclerosis, myocardial infarction, and angina. Thus, a treatment needs to be developed so that tissue damage caused by a low-oxygen state or low-nutrient state due to the non-formation of blood vessels may be reduced, and angiogenesis may be induced or promoted for smooth tissue regeneration.

Particularly, angiogenesis must be accompanied by a wound healing process necessary for regenerating wounded skin tissue. At a beginning stage of the wound, an inflammatory reaction caused by necrosis of cells and rupture of blood vessels occurs, and a series of processes of forming a biological medium material, such as callicrein, thrombin, or plasmin, may be followed after the inflammatory reaction along with a phenomenon of leaking out blood components, activation of platelets, and blood coagulation.

A treatment of physiological diseases using angiogenesis is referred to as an angiogenesis treatment, which is known as being effective in treating an angiogenesis-dependent ailment selected from the group consisting of a wound, chronic ulcer, ischemic stroke, myocardial infarction, angina pectoris, and cerebrovascular dementia. (KR 2009-0010662).

An angiogenesis promoting factor such as a vascular endothelial growth factor (VEGF) is already used as a medication for severe anemia. Also, angiogenesis promoting factors, such as a fibroblast growth factor, an epidermal growth factor, a platelet-derived epidermal growth factor, or the like, have been studied for clinical treatments. However, the factors are proteins that are difficult to be separated or purified and are expensive and thus are difficult to be clinically applied.

VEGF is a typical protein controlling angiogenesis. VEGF combines with a VEGF receptor 1, 2, or 3 (VEGFR1, VEGFR2, or VEGFR3) present in vascular endothelial cells, induces phosphorylation of tyrosine present in the VEGF receptor, and brings about activation of the vascular endothelial cells, thus consequently VEGF has a profound effect on the process of angiogenesis. Phosphorylation in VEGFR2 serves as the most important receptor in an angiogenesis signal transduction mechanism. Among medications using VEGF as a target, the most typical medication that is clinically used is Avastin, which corresponds to a VEGF neutralizing antibody and is approved by the FDA.

Heat shock protein (HSP) 27, which is a protein with a low molecular weight and has a charperon activity, self-aggregates to form clusters with respect to external environment factors, such as free radicals, heat, toxins, or the like, and thus has a defense ability to the external environment factors (NCBI Gene Bank Accession Number: NP_001531.1). Secretion of HSP 27 with a low molecular weight (HSP27 is produced in a human, and HSP25 is produced in a rat) has been confirmed by the present inventors. Many functions of HSP27 are known; for example, the HSP27 combines with a protein inducing apoptosis of cancer cells and increases resistance of cancer cells to radiation and anticancer drugs (Oncogene. May 26, 2005; 24(23):3715-25). However, relationships of HSP27 with VEGF, angiogenesis promotion, or wound healing promotion are not known.

DETAILED DESCRIPTION OF THE INVENTION

Technical Problem

The inventors have studied to invent a material effective in promoting angiogenesis and discovered for the first time that HSP27 inhibits growth of vascular endothelial cells by suppressing activation of VEGFR2 induced by VEGF, and thus a composition for promoting angiogenesis and a method for screening for active substances for promoting angiogenesis have been developed based on the discovery.

Thus, the present invention provides a new pharmaceutical composition for promoting angiogenesis.

The present invention also provides a pharmaceutical composition for treating an angiogenesis-dependent ailment.

The present invention also provides a method for promoting growth of vascular endothelial cells in vitro.

The present invention also provides a method for screening active substances for promoting angiogenesis.

The present invention also provides a method for screening active substances for treating an angiogenesis-dependent ailment.

Technical Solution

According to an aspect of the present invention, there is provided a pharmaceutical composition for promoting angiogenesis, the pharmaceutical composition may include an antibody that specifically binds to heat shock protein 27 (HSP27).

According to another aspect of the present invention, there is provided a pharmaceutical composition for treating an angiogenesis-dependent ailment selected from the group consisting of a wound, chronic ulcer, ischemic stroke, myocardial infarction, angina pectoris, and cerebrovascular dementia, wherein the pharmaceutical composition may include an antibody that specifically binds to HSP27.

According to another aspect of the present invention, there is provided a method of promoting growth of vascular endothelial cells in vitro by using an antibody that specifically binds to HSP27.

According to another aspect of the present invention, there is provided a method for screening for active substances for promoting angiogenesis, the method may include treating vascular endothelial cell lines with each specimen; measuring the content of HSP27 in the respective vascular endothelial cell lines; and selecting a specimen in which the HSP27 content in the vascular endothelial cell lines decreased as compared to a control group.

According to another aspect of the present invention, there is provided a method for screening for active substances for treating an angiogenesis-dependent ailment selected from the group consisting of a wound, chronic ulcer, ischemic stroke, myocardial infarction, angina pectoris, and cerebrovascular dementia, the method may include treating vascular endothelial cell lines with each specimen; measuring the content of HSP27 in the respective vascular endothelial cell lines; and selecting a specimen in which the HSP27 content in the vascular endothelial cell lines decreased as compared to a control group.

Hereinafter, an embodiment of the present invention will be described in greater detail. Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, a limited number of exemplary methods and materials are described herein. All publications mentioned herein are incorporated herein in their entirety.

As provided by the present invention, a pharmaceutical composition for promoting angiogenesis or a pharmaceutical composition for treating an angiogenesis-dependent ailment is featured in including a function inhibitor of heat shock protein 27 (HSP27) that inhibits a vascular endothelial growth factor receptor 2 (VEGFR2) phosphorylation-suppressing function of HSP27. The feature is based on the facts that VEGFR2 phosphorylation is decreased by HSP27, VEGFR2 phosphorylation is increased when a function of HSP27 is inhibited, and wound healing is promoted when a HSP27 function inhibitor is administered to a body with a wound, are first discovered by the inventor. Here, the "function inhibitor", which inhibits a VEGFR2 phosphorylation-suppressing function of HSP27, includes a material that inhibits an expression of HSP27 protein or inhibits a VEGFR2 phosphorylation-suppressing function by HSP27.

Figure 1:
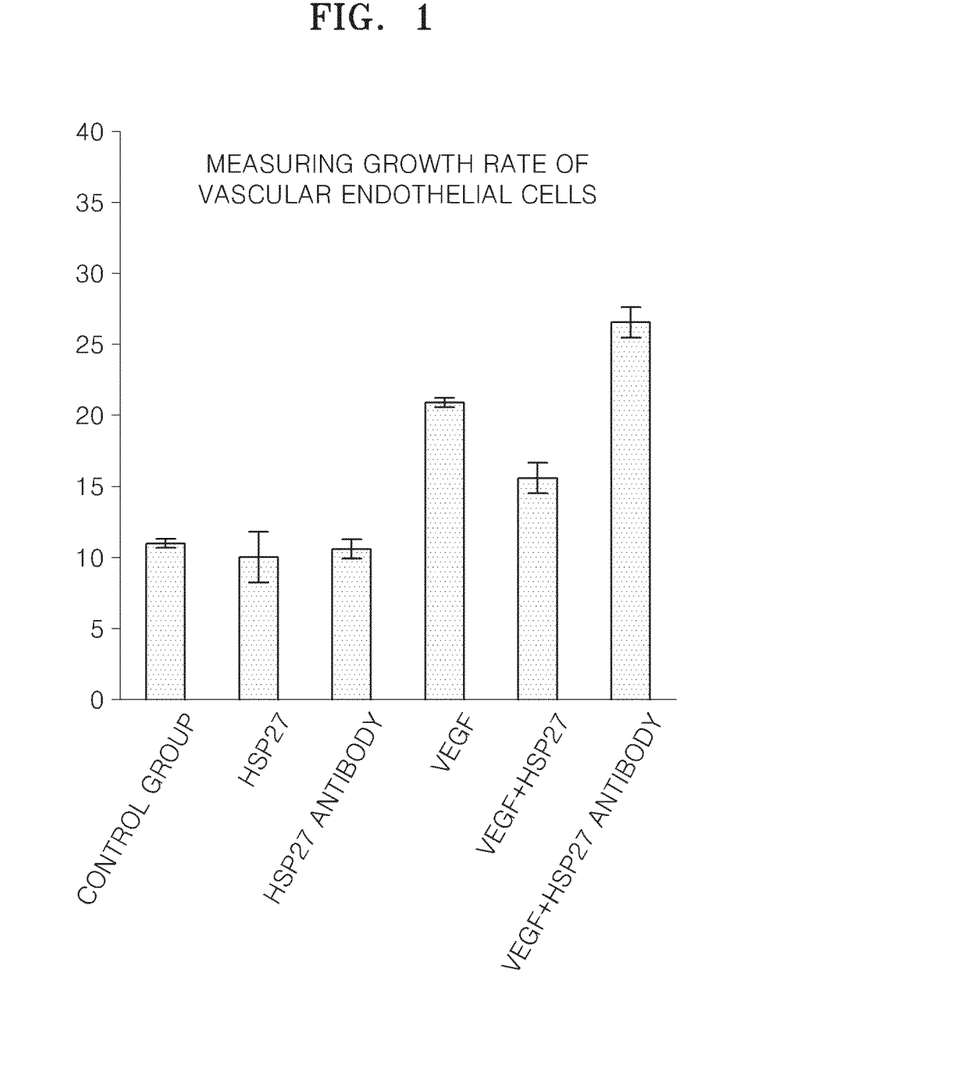
FIG. 1 is a graph showing the results of measuring changes in growth of vascular endothelial cells caused by VEGF by using a MTT proliferation assay when HUVEC was treated with HSP27 protein or HSP27 neutralizing antibody.
Figure 3:
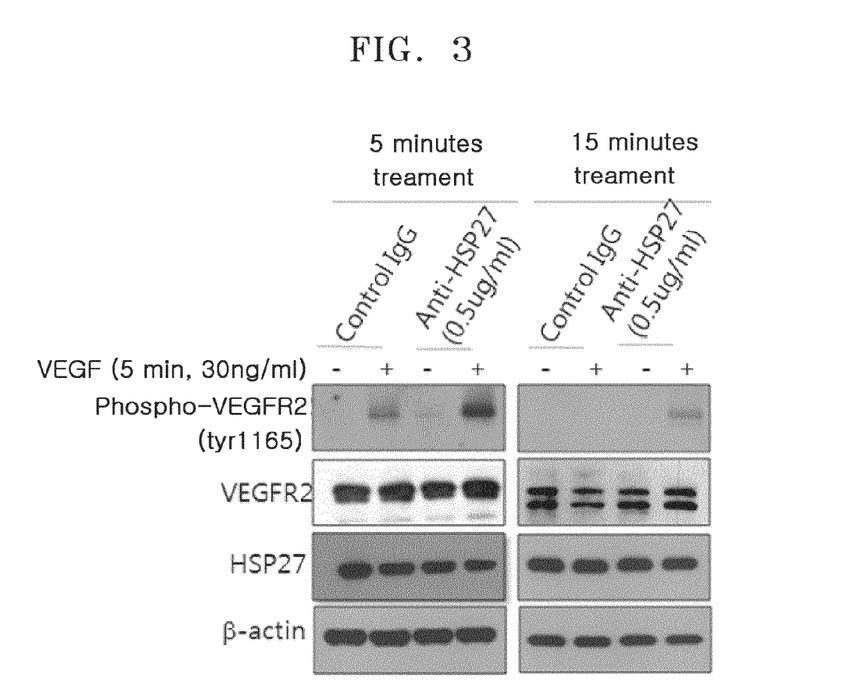
FIG. 3 is an image of the results of measuring degrees of VEGF-induced phosphorylation of VEGFR2 by using the western blotting method when HUVEC were treated with HSP27 neutralizing antibodies.
Figure 4:
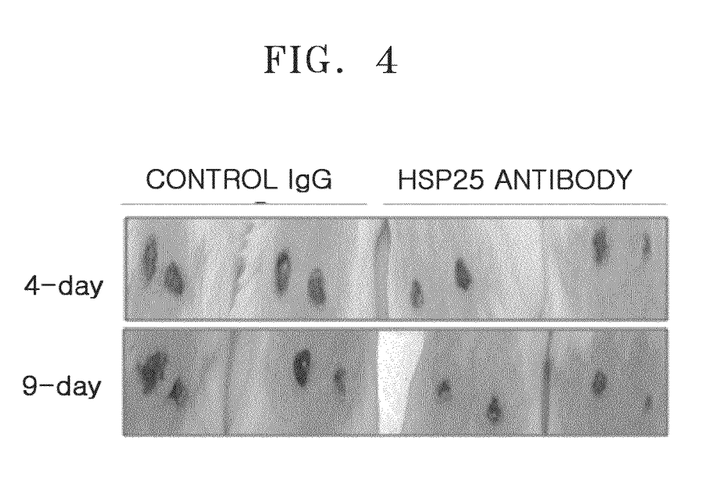
FIG. 4 show images of the results of degrees of wound healing observed with naked eyes after 4 and 9 days when IgG or mouse HSP25 neutralizing antibody is IP injected to each group of Balb/C mice wounded on their back with a punch.
Figure 5:
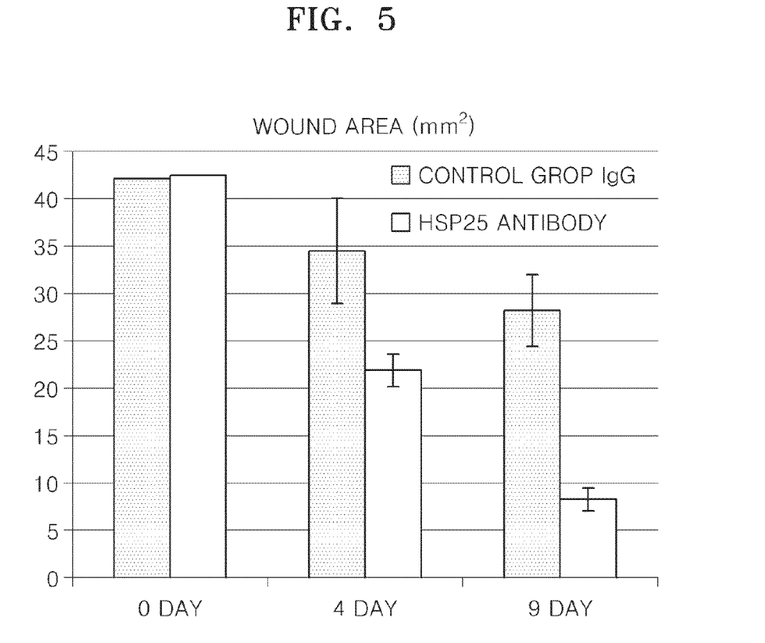
FIG. 5 is a graph showing the result of measuring areas of the wounds after 4 and 9 days when IgG or mouse HSP25 neutralizing antibody is IP injected to each group of Balb/C mice wounded on their back with a punch.
Figure 6:
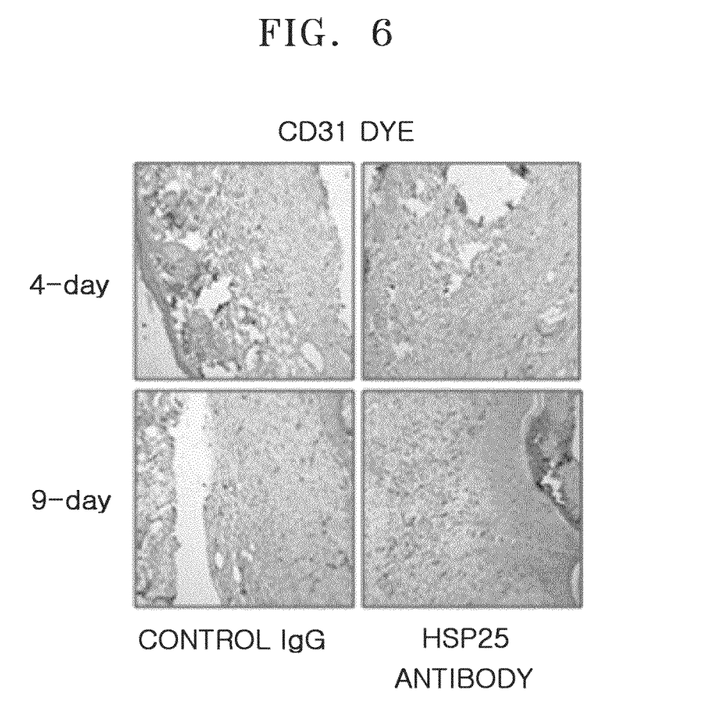
FIG. 6 is an image of the result of the blood vessel densities observed with an optical microscope after performing immunostaining and immunofluorescence staining by using PECAM-1, which is a marker of the vascular endothelial cells, on the wounded region of each group in FIG. 4.

Particularly, it is confirmed that when a human vascular endothelial cells (HUVEC) culture is solely treated with VEGF or treated with VEGF after treating with HSP27 protein or HSP27 neutralizing antibody, an increase in a growth rate of the vascular endothelial cells of a group solely treated with VEGF compared to a control group, a significant decrease in a growth rate of vascular endothelial cells of a group treated with HSP27 and VEGF combination compared to the group solely treated with VEGF, and a significant increase in a growth rate of vascular endothelial cells of a group treated with HSP27 neutralizing antibody and VEGF combination compared to the group solely treated with VEGF (FIG. 1). Also, after treating with HSP27 protein or HSP27 neutralizing antibody, the HUVEC culture was treated with VEGF, and then amounts of phospho-VEGFR2, VEGFR2, and HSP27 were measured. As a result, in the case of the HSP27 protein-treated group, an amount of phospho-VEGFR2 significantly decreased compared to the control group (administered with IgG), and amounts of VEGFR2 and HSP27 had almost no change (FIG. 2), and in the case of the HSP27 neutralizing antibody-treated group, an amount of phospho-VEGFR2 significantly increased compared to the control group (administered with IgG), and amounts of VEGFR2 and HSP27 had almost no change (FIG. 3). Also, as a result of intraperitoneal (IP) injection of HSP25 neutralizing antibody to a mouse with a wound on its back, it was confirmed that a size of the wound reduced to ⅓ or less compared to the control group (administered with IgG) (FIGS. 4 and 5). Moreover, an amount of the vascular endothelial cells distributed around the scar of the mouse was measured, and as a result, it was confirmed that a significantly greater number of vascular endothelial cells distributed in the HSP27 neutralizing antibody-treated group compared to the control group (FIG. 6).

Therefore, unlike in the case of HSP27, which inhibited a growth of vascular endothelial cells, it may be confirmed from the results of the experiments that a function inhibitor of HSP27 (e.g., HSP27 neutralizing antibody) promotes a growth of vascular endothelial cells. That is, such a promotion may be caused by the function inhibitor of HSP27 promoting phosphorylation of VEGFR2 as HSP27 suppresses phosphorylation of VEGFR2. Thus, the function inhibitor of HSP27 that is a material inhibiting expression of HSP27 protein or inhibiting a VEGFR2 phosphorylation-suppressing function of HSP27 has an activity in angiogenesis promoting or treating angiogenesis-dependent ailments.

In this respect, the present invention provides a pharmaceutical composition for promoting angiogenesis including a HSP27 function inhibitor based on the results of the experiments. Also, the present invention provides a pharmaceutical composition for treating an angiogenesis-dependent ailment selected from the group consisting of a wound, chronic ulcer, ischemic stroke, myocardial infarction, angina pectoris, and cerebrovascular dementia.

The HSP27 function inhibitor includes a material that inhibits a VEGFR2 phosphorylation-suppressing function of HSP27 or inhibits an expression of HSP27 protein. Examples of the HSP27 function inhibitor include an anti-sense oligonucleotide directed against HSP27 genes, an HSP27-targeted siRNA, an inhibitor of phosphorylation-suppressing function with respect to VEGFR2 of HSP27, and the like.

In the present invention, a pharmaceutical composition including an anti-sense oligonucleotide directed against HSP27 genes that inhibit expression of HSP27 is provided. The pharmaceutical composition includes an initiation codon region of the HSP27 genes, a coding region, and an oligonucleotide that is anti-sense to regions inside 2 to 10 nucleotides at a 5' or 3' intron-exon junction, or anti-sense to mRNA which is complementary to the genes.

Use of siRNA to treat diseases by inhibiting gene expression has been widely studied. Thus, the present invention provides a pharmaceutical composition for healing wounds including HSP27-targeting siRNA. HSP27-targeting siRNA may be appropriately designed by finding a target area in the genes with reference to a commonly known method in the art. The HSP27-targeting siRNA included in the pharmaceutical composition of the present invention includes a separated siRNA including a short double-stranded RNA constructed with about 15 to about 30 nucleotides, preferably about 19 to about 25 nucleotides, that target a target mRNA. The HSP27-targeting siRNA includes an anti-sense RNA strand that is complementary to a sense RNA strand. The sense and anti-sense RNA strands in the HSP27-targeting siRNA of the present invention may include two single-stranded RNA molecules that are complementary to each other, a single molecule, wherein two complementary regions form a base pair, and each complementary region is covalently bonded by a single hairpin region of the single molecule.

The siRNA included in the present invention may be obtained by using many techniques known to one of ordinary skill in the art. For example, the siRNA may be produced by using a chemical synthesis or recombination method that is commonly known in the art.

An effective dose of the anti-sense oligonucleotide and siRNA of the present invention to be administered to a subject may be easily determined by considering factors such as size, weight, degree of disease progression, age, physical condition, gender, route of administration, and local or systemic administration. In general, an effective dose of the anti-sense oligonucleotide and siRNA of the present invention includes an intercellular concentration in a range of about 1 nM to about 100 nM at a disease area or an area nearby the disease area. The effective dose may be increased or reduced than said intercellular concentration according to the need. The anti-sense oligonucleotide or the siRNA of the present invention may be administered to a subject as itself by mixing the sense oligonucleotide or the siRNA with a delivery agent or as a recombinant plasmid or a virus vector that expresses the anti-sense oligonucleotide or siRNA. Examples of an appropriate delivery agent include lipofectin, lipofectamine, cellfectin, polymer cation (e.g., polylysin), and liposome. The pharmaceutical composition including the anti-sense oligonucleotide and siRNA of the present invention may be delivered into cells using a gene gun, ultrasound, or electric shock.

HSP27 suppresses phosphorylation of VEGFR2 and thus drops proliferation of vascular endothelial cells and angiogenesis. Thus, the present invention provides a pharmaceutical composition for promoting angiogenesis including an inhibitor with respect to a VEGFR2 phosphorylation suppressing function of HSP27 protein. Also, the present invention provides a pharmaceutical composition for treating an angiogenesis-dependent ailment selected from the group consisting of a wound, chronic ulcer, ischemic stroke, myocardial infarction, angina pectoris, and cerebrovascular dementia.

The inhibitor with respect to a VEGFR2 phosphorylation suppressing function of HSP27 protein includes any material that inhibits HSP27 protein from suppressing VEGFR2 phosphorylation, the inhibitor including a typical antibody that specifically binds to HSP27 protein.

The term "antibody" as used herein refers to a specific protein molecule indicated for an antigenic area. The antibody used in the present invention may be a monoclonal, or polyclonal antibody, an immunologically active fragment (e.g., Fab or $(Fab)_2$ fragment), a heavy-chain antibody, a humanized antibody, a light-chain antibody, a gene manipulated single-strand Fv molecule, a chimeric antibody, or the like.

Since HSP27 is a commonly known protein (NCBI Gene Bank Accession Number: NP_001531.1), the antibody used in the present invention may be manufactured by using HSP27 protein as an antigen using a commonly method known in the art of immunology. HSP27 protein which is used as an antigen of the antibody according to the present invention may be extracted or synthesized from natural resources and may be manufactured by using a recombination method based on DNA sequences. When a gene recombination skill is used, a nucleic acid coding a protein is inserted in an appropriate expression vector, the recombinant expression vector is transformed into host cells, and the transformant are cultured to express the targeted protein, and then the targeted protein may be collected from the transformant, thereby obtaining the antibody.

For example, a polyclonal antibody may be produced by using a method of obtaining a blood serum including the antibody by injecting a protein antigen to an animal and drawing blood from the animal. The antibody may be produced from many endothermic animals such as horses, cows, goats, sheep, dogs, chickens, turkeys, rabbits, mice, or rats.

A monoclonal antibody may be manufactured by using a commonly known fusion method (Kohler and Milstein, European J. Immunol. 6: 511-519 1976), a recombinant DNA method (U.S. Pat. No. 4,816,567), and a phage antibody library (Clackson et al., Nature, 352, 624-628, 1991; Marks et al., J. Mol. Biol. 222, 58:1-597, 1991). Also, a monoclonal antibody of HSP27 may be manufactured by using the known method stated above, or a commercially available monoclonal antibody of HSP27 (SPA-800, available from Stressgen, Canada) may be purchased and be used.

The pharmaceutical compositions of the present invention may be administered by being formulated as a formulation for topical administration or an injection according to a common method known in the pharmaceutical field.

The formulation for topical administration or injection may be manufactured according to an injection manufacturing method commonly known in the art.

The formulation for topical administration includes a liquid phase or semi-liquid phase formulation appropriate for penetration to a treatment-needed area through the skin. An example of the liquid phase formation may be a topical solution, but is not limited thereto. Examples of the semi-liquid phase formulation may be liniment, lotion, cream, ointment, paste, gel, emugel, or the like, but are not limited thereto. The pharmaceutical formulations are commonly used and commonly known to one of ordinary skill in the art of pharmaceutical formulations.

The topical solution of the present invention may be manufactured as a watery or oily solution or a suspension. This formulation may be manufactured by dissolving a pharmaceutical compound in an appropriate watery solution of a bactericidal agent, fungicide, and/or an appropriate preserving agent preferably including a surfactant. A solvent appropriate for manufacturing an oily solution may include glycerol, diluted alcohol, or propylene glycol.

The lotion and liniment according to the present invention include a sterilized watery solution and a solution selectively containing germicide that is appropriate to be applied to the skin. Also, the lotion and liniment may include a formulation that promotes drying and cooling the skin, such as alcohol or acetone, and/or a humectant, such as glycerol or oil such as castor oil or peanut oil.

The cream, ointment, or paste is a semi-solid formulation. The semi-solid formulation may be manufactured solely or as a solution or suspension in watery or non-watery fluid with a help of an appropriate machine in addition to an oily or non-oily base by mixing a finely divided salt or a powder-type of salt that is pharmaceutically available. The base may include a hydrocarbon. Examples of the hydrocarbon may be a hard, soft, or liquid paraffin, glycerol, wax, metal soap, mucus, a natural oil (e.g., almond oil, corn oil, peanut oil, or olive oil), wool fat, derivatives thereof, and/or fatty acid (e.g., stearic acid or oleic acid), but are not limited thereto. The formulation may contain a surfactant, such as a cationic, anionic, or non-ionic surfactant. Examples of the surfactant may be sorbitan ester or a polyoxyethylene derivative thereof (e.g., polyoxyethylene fatty acid ester), and a carboxymethylene derivative thereof (e.g., carbopol). The formulation may include a suspending agent such as natural gum, a cellulose derivative inorganic material such as silica, and other components such as lanolin. In a case of the ointment, polyethylene glycol 540, polyethylene glycol 3350, and propyl glycol may also be used as mixed with the pharmaceutical compound.

The gel or emugel formulation includes any gel-forming agents that are commonly used in a pharmaceutical formulation. Examples of the gel-forming agent may be cellulose derivatives such as methyl cellulose, hydroxyethyl cellulose, and carboxymethyl cellulose; vinyl polymers such as polyvinyl alcohol and polyvinyl pyrrolidone; and carboxypolymethylene derivatives such as carbopol. Alternatively, another gel-forming agent that may be used in the present invention includes pectin or gum (e.g.: gum Arabic, gum tragacanth, alginate, carrageenate, agar, and gelatin). Also, the gel or emugel formulation may include additives commonly used in a type of formulation, such as preservatives, antioxidants, stabilizing agents, coloring agents, or aromatics.

The excipients and additives used in the formulations as mentioned above and a method of preparing the formulations may be selected and prepared according to a widely known method in the art (e.g., methods disclosed in the latest version of Remington's Pharmaceutical Science).

An dose and time for administering the pharmaceutical composition of the present invention depend on age, gender, physical condition, and weight of a subject to be administered, route and number of administrations, and a formulation of drug. An amount of administration per day may be in a range of about 0.01 ug/kg to about 10 g/kg, and preferably, in a range of about 0.01 mg/kg to about 100 mg/kg.

When the pharmaceutical composition of the present invention is used as a gene therapeutic agent, the nucleic acid may be directly injected to a subject or a carrier (vector) including the nucleic acid may be administered to a subject. In a case of nucleic acid molecules, a dose depends on an expression vector, a subject to be administered, or the like. In a case of a virus vector, an amount of recombination virus including the virus vector is in a range of about $10^3$ pfu/kg to about $10^{12}$ pfu/kg. Also, the nucleic acid may be delivered using liposome, virus, gene gun, polymer, ultrasound, or electric shock.

According to the present invention, an HSP27 antibody blocks suppression of VEGFR2 phosphorylation of HSP27 and promotes growth of vascular endothelial cells, thus the HSP27 antibody may be used to promote growth of vascular endothelial cells.

Thus, according to another aspect of the present invention, a method for promoting the in vitro growth of endothelial cells using an antibody that specifically binds to HSP27 is provided.

The antibody that specifically binds to HSP27 may be the antibody described above, and the promotion of vascular endothelial cell growth may be enabled by simply adding the antibody that specifically binds to HSP27 to the vascular endothelial cells desired to grow.

Also, according to the present invention, HSP27 protein suppresses VEGFR2 phosphorylation, and reduces angiogenesis, thus active substances for promoting angiogenesis may be screened by selecting a material that reduces expression of HSP27 among unknown materials.

Therefore, according to another aspect of the present invention, a method for screening for active substances for promoting angiogenesis based on a discovery that HSP27 protein inhibits angiogenesis by suppressing VEGFR2 phosphorylation is provided.

The method for screening for active substances for promoting angiogenesis includes treating vascular endothelial cell lines with each specimen; measuring the content of HSP27 in the respective vascular endothelial cell lines; and selecting a specimen in which the HSP27 content in the vascular endothelial cell lines decreased as compared to a control group.

Also, according to another aspect of the present invention, a method for screening for active substances for treating an angiogenesis-dependent ailment selected from the group consisting of a wound, chronic ulcer, ischemic stroke, myocardial infarction, angina pectoris, and cerebrovascular dementia based on a discovery that HSP27 protein inhibits angiogenesis by suppressing VEGFR2 phosphorylation, is provided.

The method for screening for active substances for treating an angiogenesis-dependent ailment includes treating vascular endothelial cell lines with each specimen; measuring the content of HSP27 in the respective vascular endothelial cell lines; and selecting a specimen in which the HSP27 content in the vascular endothelial cell lines decreased as compared to a control group.

The content of HSP27 may be determined by, for example, measuring an amount of mRNA of HSP27 by using a Northern blot method or measuring an amount of expressed HSP27 protein by using an antibody with respect to a HSP27 protein, and the method may be any known method in the art.

Advantageous Effects

As described above, a function inhibitor of HSP27, which is a material inhibiting expression of HSP27 or inhibiting a function of HSP27 suppressing of VEGFR2 phosphorylation according to an aspect of the present invention is effective in promoting angiogenesis, and the function inhibitor is effective in treating an angiogenesis-dependent ailment selected from the group consisting of a wound, chronic ulcer, ischemic stroke, myocardial infarction, angina pectoris, and cerebrovascular dementia due to the angiogenesis promoting effect. Also, active substances for promoting angiogenesis and active substances for treating angiogenesis-dependent ailments may be screened by measuring changes in an amount of HSP27. The technology according to the present invention is an advanced technology that discovers new medical targets by systemic study of signal transfer between proteins in cells and the signal mapping.

EXAMPLES

Hereinafter, membranes for alveolar bone regeneration according to exemplary embodiments of the present invention will be described in greater detail with reference to the attached drawings.

Experimental Method

1) Culture of cell lines to be used: Human vascular endothelial cells (HUVEC) bought from Lonza were cultured in a culture chamber at a temperature of 37° in a 5% CO2 condition using an endothelial growth medium (EGM) including various growth factors necessary for growth of the vascular endothelial cells.

2) Proliferation assay of vascular endothelial cells: The cells were distributed in a 24-well dish with 7000 cells per well and cultured at 37° C. in $CO_2$ for 24 hours.

Opti-MEM (available from GIBGO) including 1% fetal bovine serum (FBS)(available from GIBGO) was treated with 1 ug/ml of HSP27 (available from Stressgen, Canada) or 0.5 ug/ml HSP27 neutralizing antibody (available from Stressgen, Canada) for an hour, 30 ng/ml VEGF was added thereto, and then on the third day, MTT assay was performed in the following manner: First, the medium was removed, the cells were washed with a PBS buffer solution twice, and then 100 ul of 5 mg/ml MTT (Thiazolyl Blue Tetrazolium Bromide) solution was added to each well and allowed to react at 37° C. for 4 hours. After removing the MTT solution, 200 ul of 4 mM HCl solution was added to the cells, then the solution was shaken in Shaker for 15 minutes to allow the reaction to occur, and light absorptivity was measured in a contrast wavelength range of about 620 nm to about 590.

3) Protein analysis using electrophoresis and immune response: To analyze protein in the sample, polyacrylamide gel electrophoresis (PAGE) was first performed, and then a western blot was performed. The sample cells were suspended in a dissolution solution of 120 mM NaCl, 40 mM Tris (pH 8.0), and 0.1% NP40 to burst the cells. Next, a predetermined amount of proteins was segregated according to their molecular weights by 10% SDS-PAGE, and then the proteins were moved to a nitrocellulose membrane and analyzed by immunoblotting analysis.

4) Animal experiment model of wound healing: Wounds were created on the back of each 8-week old male Balb/C mice using a punch with a diameter of 6.5 mm. 40 mg/kg of IgG (available from Sigma) and HSP27 neutralizing antibody were each respectively intraperitoneally (IP) injected to the control group and experimental group of mice every other day, and sizes of the wounds were observed.

5) Tissue immunostaining: Tissues of the wounded regions of the mice were fixed with formalin for one day, and paraffin sections were prepared. The tissues were sequentially immersed in xylene, 95%, 90%, and 70% ethanol solutions to remove paraffin, reacted with 3% hydrogen peroxide for 15 minutes, and reacted with a CD31 antibody (available from Santacruz) in a PBS (including 0.1% Triton 1-100) solution at a ratio of 1:100 at room temperature for an hour or more. As a secondary antibody, a biotinylated secondary antibody (available from Zymed) was added to react for 30 minutes, then streptavidin-HRP (available from Zymed) was added to react for 15 minutes, and 3,3'-Diaminobenzidine (DAB) was added to react. After 3 minutes, when the tissues appeared to be brown, the tissues were washed with the PBS to stop the reaction, and the tissues were immersed into hematoxyline for 5 minutes to stain nuclear. Next, the tissues were washed with running water and sequentially immersed in 70%, 90%, 95% ethanol solutions, and a xylene solution, and then one drop of glycerol was dropped on the tissues, and the tissues were covered with a cover slide to be observed with a microscope (available from Carl Zeiss Vision).

Example 1

Confirmation of Growth Promotion of Vascular Endothelial Cells of HSP Neutralizing Antibody Human vascular endothelial cell (HUVEC) lines were treated with 1 ug/ml HSP27 protein or 0.5 ug/ml HSP27 neutralizing antibody for an hour and then treated with 30 ng/ml of human vascular endothelial growth factor (VEGF). After 3 days, degrees of cell growth were measured with the MTT analyzing method. The results of the degrees of cell growth of a HSP27 solely-treated group, a HSP27 neutralizing antibody solely-treated group, a VEGF solely-treated group, a VEGF and HSP27 combined-treated group, and a VEGF and HSP27 neutralizing antibody combined-treated group are shown in FIG. 1.

FIG. 1 is a graph showing the results of measuring changes in growth of vascular endothelial cells caused by VEGF by using a MTT proliferation assay when HUVEC was treated with HSP27 protein or HSP27 neutralizing.

Referring to FIG. 1, a growth rate of vascular endothelial cells of the VEGF and HSP27 combined-treated group was lower than that of the VEGF solely-treated group. A growth rate of vascular endothelial cells of the VEGF and HSP27 neutralizing antibody combined-treated group was significantly increased than that of the VEGF solely-treated group. Each of the HSP27 solely-treated group and HSP27 neutralizing antibody solely-treated group did not show any change in its growth rate of vascular endothelial cells.

Example 2

Confirmation of Promoting Effect of VEGFR2 Phosphorylation of HSP27 Neutralizing Antibody HUVEC lines were treated with 1 ug/ml HSP27 protein or 0.5 ug/ml HSP27 neutralizing antibody for an hour and then treated with 30 ng/ml of human VEGF for 5 minutes. Then, the cells were fractioned, and a western blotting was performed using phospho-VEGFR2, VEGFR2, and HSP27 neutralizing antibody (available from Stressgen, Canada). The western blotting was performed using a β-actin antibody to confirm equal loading. The results of measuring phospho-VEGFR2, VEGFR2, and HSP27 in a HSP27 protein-treated group are shown in FIG. 2, and the results of measuring phospho-VEGFR2, VEGFR2, and HSP27 in a HSP27 neutralizing antibody treated group are shown in FIG. 3.

Figure 2:
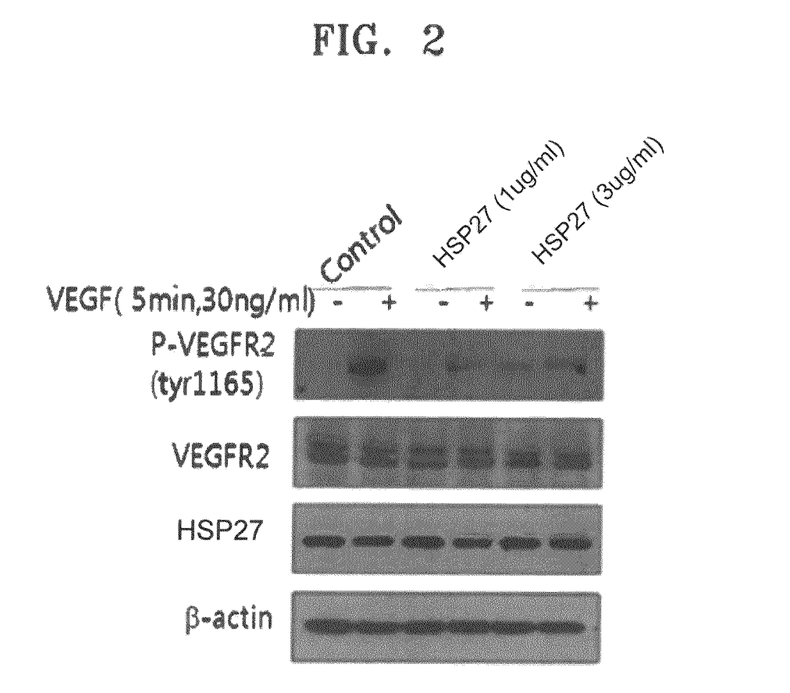
FIG. 2 is an image of the results of measuring degrees of VEGF-induced phosphorylation of VEGFR2 by using a western blotting method when HUVEC were treated with HSP27 proteins.

FIG. 2 is an image of the results of measuring degrees of VEGF-induced phosphorylation of VEGFR2 by using the western blotting method when HUVEC were treated with HSP27 proteins.

FIG. 3 is an image of the results of measuring degrees of VEGF-induced phosphorylation of VEGFR2 when HUVEC were treated with HSP27 neutralizing antibodies.

Referring to FIG. 2, when the cells were pre-treated with 1 ug/ml and 3 ug/ml HSP27 proteins, it was confirmed that VEGF-induced phosphorylation of VEGFR2 was significantly decreased. On the other hand, the amounts of VEGFR2 expression and HSP27 expression were not affected.

Referring to FIG. 3, when the cells were pre-treated with HSP27 neutralizing antibody, it was confirmed that VEGF-induced phosphorylation of VEGFR2 was significantly increased. On the other hand, the amounts of VEGFR2 expression and HSP27 expression were not affected.

Example 3

Increase of Wound Healing Effect Caused by HSP25 Neutralizing Antibody in Animal Model Wounds were created on the back of Balb/C mice using a punch, and IgG (available from Stressgen, Canada) or mouse HSP25 neutralizing antibody (available from Stressgen, Canada) was IP injected to each group of mice, and a degree of wound healing was observed with naked eyes after 4 and 9 days, and the results were photographed. The results of the photographs are shown in FIGS. 4 and 5.

FIG. 4 show images of the results of degrees of wound healing observed with bare eyes after 4 and 9 days when IgG or mouse HSP25 neutralizing antibody is IP injected to each group of Balb/C mice wounded on their back with a punch.

FIG. 5 is a graph showing the result of measuring areas of the wounds after 4 and 9 days when IgG or mouse HSP25 neutralizing antibody is IP injected to each group of Balb/C mice wounded on their back with a punch.

Referring to FIGS. 4 and 5, when the mice were treated with HSP25 neutralizing antibody, it was shown that the sizes of the wounds were reduced to ⅓ or less after 9 days compared to the control group.

Example 4

Confirmation of Vascular Endothelial Cells Density when Animal Model is Treated with HSP25 Neutralizing Antibody Degrees of blood vessel density were observed with an optical microscope after performing immunostaining and immunofluorescence staining according to an immunohistochemistry method by using PECAM-1, which is a marker of the vascular endothelial cells, on the wounded region of the mice of Example 3. The results of the optical microscope observation are shown as photographs in FIG. 6.

FIG. 6 is an image of the result of the blood vessel densities observed with an optical microscope after performing immunostaining and immunofluorescence staining by using PECAM-1, which is a marker of the vascular endothelial cells, on the wounded region of each of the groups in FIG. 4.

Referring to FIG. 6, when the cells were treated with HSP25 neutralizing antibody, the cells stained with PECAM-1 appeared more around the wounded region compared to the control group. Also, when treated with HSP25 neutralizing antibody, more blood vessels appeared as stained in brown by PECAM-1.

Thus, it may be confirmed that HSP27 neutralizing antibody increases activity of VEGFR2 induced by VEGF and promotes a process of angiogenesis, thus increases an efficiency of wound healing.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method for promoting angiogenesis, the method comprising administering to a subject in need thereof an effective amount of a pharmaceutical composition comprising an antibody that specifically binds to heat shock protein 27 (HSP27) and wherein the antibody, in the presence of VEGF, promotes vascular endothelial growth factor (VEGF)-induced phosphorylation of vascular endothelial growth factor receptor 2 (VEGFR2), thereby promoting angiogenesis.

2. A method of increasing efficiency of wound healing, the method comprising administering to a subject in need thereof an effective amount of a pharmaceutical composition comprising an antibody that specifically binds to heat shock protein 27 (HSP27).

3. The method of claim 1, wherein the antibody is a polyclonal antibody or monoclonal antibody.

4. The method of claim 1, wherein administering comprises administration by injection.

5. The method of claim 1, wherein administering comprises topical administration.

6. The method of claim 5, wherein topical administration is in the dosage form of a solution, a gel, an emugel, a cream, an ointment or a lotion.

7. A method of promoting growth of vascular endothelial cells in vitro comprising contacting vascular endothelial cells in vitro with an antibody that specifically binds to heat shock protein 27 (HSP27) and wherein the antibody, in the presence of VEGF, promotes vascular endothelial growth factor (VEGF)-induced phosphorylation of vascular endothelial growth factor 2 (VEGFR2), thereby promoting growth of the vascular endothelial cells.

8. The method of claim 7, wherein the antibody is a polyclonal antibody or monoclonal antibody.

* * * * *